(12) United States Patent
Lakso et al.

(10) Patent No.: US 11,471,338 B2
(45) Date of Patent: Oct. 18, 2022

(54) ABSORBENT ARTICLE

(71) Applicant: Essity Hygiene and Health Aktiebolag, Gothenburg (SE)

(72) Inventors: Elisabeth Lakso, Gothenburg (SE); Thor Egill Gardarsson, Sandsjöfors (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/646,827

(22) PCT Filed: Oct. 3, 2017

(86) PCT No.: PCT/SE2017/050967
§ 371 (c)(1),
(2) Date: Mar. 12, 2020

(87) PCT Pub. No.: WO2019/070171
PCT Pub. Date: Apr. 11, 2019

(65) Prior Publication Data
US 2020/0276061 A1 Sep. 3, 2020

(51) Int. Cl.
*A61F 13/15* (2006.01)
*A61F 13/49* (2006.01)
(Continued)

(52) U.S. Cl.
CPC .... *A61F 13/4902* (2013.01); *A61F 13/49012* (2013.01); *A61F 13/49015* (2013.01)

(58) Field of Classification Search
CPC .......... A61F 13/15; A61F 13/47; A61F 13/53; A61F 13/51; A61F 13/4902;
(Continued)

(56) References Cited

U.S. PATENT DOCUMENTS

| 4,610,681 A | * | 9/1986 | Strohbeen | ......... A61F 13/49011 |
| | | | | 604/396 |
| 4,619,649 A | * | 10/1986 | Roberts | ................. A61F 13/496 |
| | | | | 604/385.29 |

(Continued)

FOREIGN PATENT DOCUMENTS

| CN | 101208063 A | 6/2008 |
| CN | 101257872 A | 9/2008 |

(Continued)

OTHER PUBLICATIONS

Office Action (Notification of the First Office Action) dated Sep. 23, 2020 by the China National Intellectual Property Administration (CNIPA) of the People's Republic of China in corresponding Chinese Patent Application No. 201780094502.7, and an English Translation of the Office Action. (12 pages).

(Continued)

*Primary Examiner* — Tatyana Zalukaeva
*Assistant Examiner* — Ilya Y Treyger
(74) *Attorney, Agent, or Firm* — Buchanan Ingersoll & Rooney PC

(57) ABSTRACT

An absorbent article having a front panel, a rear panel, an intermediate panel joining the front and the rear panels and optionally one or more fitting components is provided. At least one of the panels and/or the fitting components is elastically contractible and made of an elastic nonwoven material that is pre-stretched and has both non-elastic and elastic polymeric material components in the form of fibers. The nonwoven material is bonded by individual bonding points arranged in a pattern. The pattern has rows of individual bonding points extending in a machine-direction and a cross-direction of the nonwoven material, and each has a centre point. The centre point of each bonding point in a row of bonding points extending in the cross-direction and/or machine-direction is offset from a centre point of each (Continued)

bonding point in a neighbouring row of bonding points extending in the cross-direction and/or in the machine-direction, respectively.

32 Claims, 7 Drawing Sheets

(51) Int. Cl.
    *A61F 13/47*     (2006.01)
    *A61F 13/53*     (2006.01)
    *A61F 13/51*     (2006.01)
    *C08L 77/00*     (2006.01)
    *A01K 23/00*     (2006.01)
    *A47L 13/17*     (2006.01)

(58) Field of Classification Search
    CPC ......... A61F 13/49012; A61F 13/49015; C08L 77/00; A01K 23/00; A47L 13/17
    See application file for complete search history.

(56) References Cited

U.S. PATENT DOCUMENTS

| | | | |
|---|---|---|---|
| 4,747,846 A * | 5/1988 | Boland | A61F 13/49007 604/385.22 |
| 4,909,804 A * | 3/1990 | Douglas, Sr. | A61F 13/4963 604/385.29 |
| 5,236,430 A * | 8/1993 | Bridges | B29C 66/723 604/358 |
| 5,779,831 A * | 7/1998 | Schmitz | B29C 66/135 156/227 |
| 6,069,097 A | 5/2000 | Suzuki et al. | |
| 2005/0033257 A1 | 2/2005 | Miyoshi et al. | |
| 2007/0005038 A1 | 1/2007 | Mansfield et al. | |
| 2007/0032771 A1 | 2/2007 | Abed et al. | |
| 2011/0196327 A1 | 8/2011 | Chhabra et al. | |
| 2012/0277703 A1 | 11/2012 | Rhein et al. | |
| 2012/0317997 A1 | 12/2012 | Pozivil et al. | |
| 2015/0088088 A1 | 3/2015 | Wade et al. | |
| 2015/0164705 A1 | 6/2015 | Thomas et al. | |

FOREIGN PATENT DOCUMENTS

| | | | |
|---|---|---|---|
| CN | 103501741 A | | 1/2014 |
| CN | 105555240 A | | 5/2016 |
| DE | 1 876 275 A1 | * | 1/2008 |
| EP | 1876275 A1 | | 1/2008 |
| EP | 2581069 A1 | | 4/2013 |
| JP | 09117982 A | | 5/1997 |
| JP | 2007-138374 A | | 6/2007 |
| JP | 2008-541867 A | | 11/2008 |
| JP | 2013-507585 A | | 3/2013 |
| JP | 2013-518698 A | | 5/2013 |
| JP | 2014-510589 A | | 5/2014 |
| RU | 2322222 C2 | | 4/2008 |
| WO | 9621760 A1 | | 7/1996 |
| WO | 2012134988 A1 | | 10/2012 |

OTHER PUBLICATIONS

International Preliminary Report on Patentability for International Application No. PCT/SE2017/050967, dated Oct. 8, 2019, 11 pages.
International Search Report and Written Opinion for International Application No. PCT/SE2017/050967, dated May 16, 2018, 13 pages.
Office Action (Decision to Grant) dated Nov. 24, 2020, by the Federal Service for Intellectual Property in Russian Patent Application No. 2020115081/03(024997) and an English Translation of the Office Action. (21 pages).
Office Action (Notice of Reasons for Rejection) dated Jun. 7, 2021, by the Japanese Patent Office in corresponding Japanese Patent Application No. 2020-519086, and an English Translation of the Office Action. (6 pages).
Extended European Search Report issued in corresponding European Patent Application No. 17 92 8001 (5 pages).

* cited by examiner

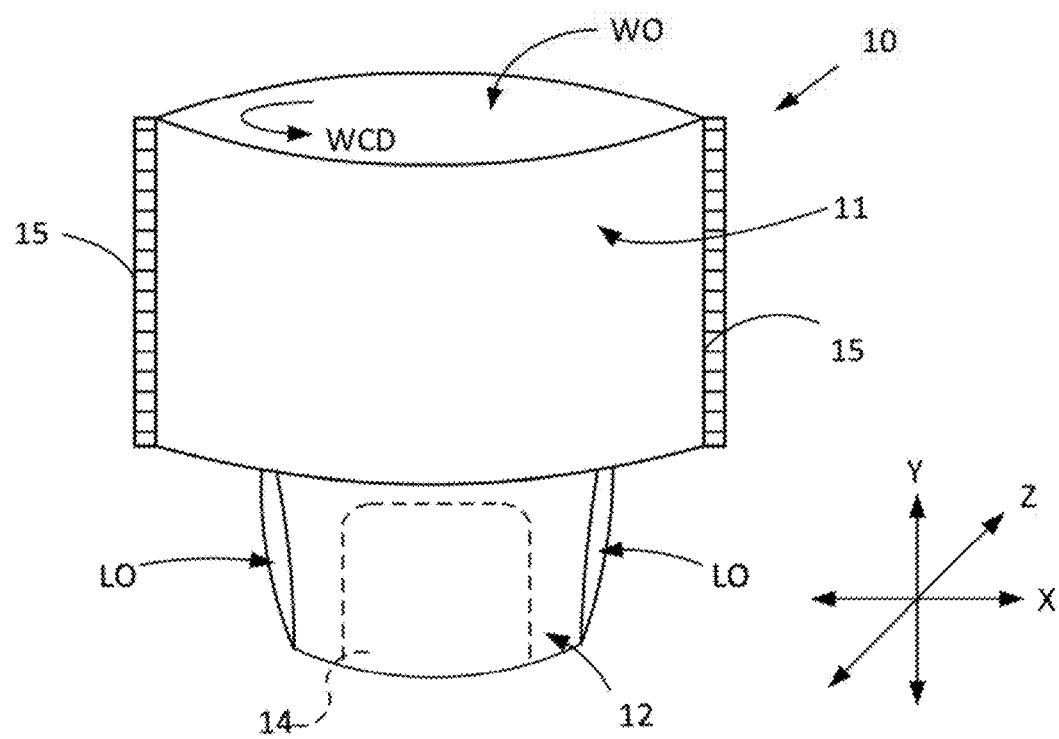
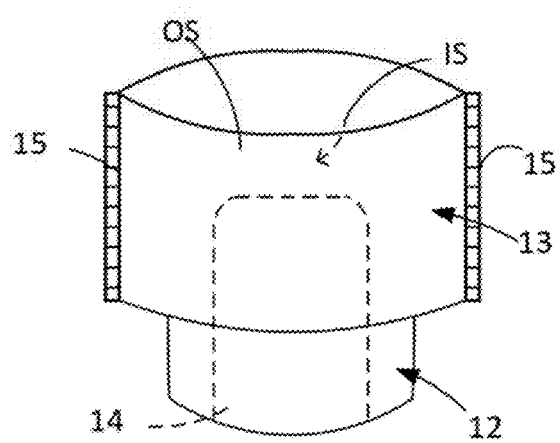 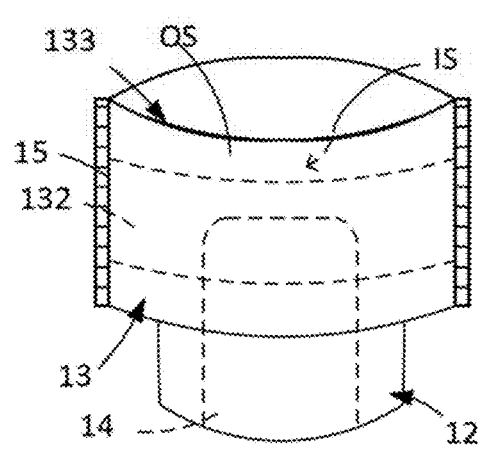
Fig. 1a
Fig. 1b  Fig. 1c

ABSORBENT ARTICLE

CROSS REFERENCE TO RELATED APPLICATIONS

This is a U.S. National Phase application of PCT/SE2017/050967, filed Oct. 3, 2017, the disclosure of which is incorporated herein by reference in its entirety for all purposes.

TECHNICAL FIELD

The present disclosure relates an absorbent article, such as a diaper which may be a pant type diaper or open type diaper for infants or adults or an incontinence article, for male or female users.

BACKGROUND

Today there are absorbent articles, such as diapers and pant-type diaper articles in the market using activated elastic nonwoven to elastify a chassis of the article or parts thereof. Such article is previously known by for example EP2581069A1.

Despite the high standard of absorbent baby diapers available on the market today, there are still unmet needs from the consumers of ever more cloth-like and underwear-like diapers. The problem of creating more underwear-like diapers may be addressed by improving the fit of the articles for example by using an elastic stretch nonwoven as the main elastic component of the waist or belt area in the chassis of the article, instead of using for example spandex threads. Simultaneously, the materials used in the elastic components should have elastic properties to ensure a good, comfortable and snug fit, while also having soft and cloth-like haptic properties. The absorbent pant-type diaper articles on the market today can comprise elastic nonwovens in the chassis, in which typically materials based on a blend of polyurethane and polypropylene fibers are used.

Currently there are limitations and challenges related to the processing of elastic stretch nonwovens during the manufacture of absorbent articles. One challenge is the availability and supply of economically viable elastic nonwoven materials. The necessary activation step of alternate elastic stretch nonwovens requires them to have very specific designs, properties, and they must be processed under specific conditions. The activation step can easily cause holes in the material, e.g. the holes can be initiated at bond points of the material, which destroy the soft and cloth like properties of the material, or simply do not give the required elastic properties.

Thus, even though it is known to use elastic nonwoven materials in absorbent articles and these materials are functional in use, there is still a need to improve the materials so that they better manage load and stress during the manufacture of absorbent articles.

SUMMARY

An absorbent article comprising a front panel, a rear panel, an intermediate panel joining the front and the rear panels and optionally one or more fitting components for adapting the fit of the article to the body of a user. Each of the panels and fitting components have an inner surface facing, i.e. adapted to face, a wearer's skin and an outer surface facing the wearer's garment. At least one of the panels and/or the fitting components is elastically contractible and comprises an elastic nonwoven material. The elastic nonwoven material in the absorbent article is pre-stretched and comprises a non-elastic polymeric material component and an elastic polymeric material component comprised in the form of fibers. By using two components, a material which can be easily stretched while it is elastic can be obtained, which facilitates the handling of the material during manufacture of the absorbent article. The nonwoven material is bonded by means of individual bonding points arranged in a pattern, wherein the pattern comprises rows of individual bonding points extending in a machine-direction and a cross-direction of the nonwoven material. Each of the individual bonding points has a centre point and the centre point of each bonding point in a row of bonding points extending in the cross-direction and/or machine-direction is offset from a centre point of each bonding point in a neighbouring row of bonding points extending in the cross-direction and/or in the machine-direction, respectively. In this way, the bonding points can be oriented and positioned so that the bonding points may cover areas in different angles and positions whereby, the risk for hole formation during stretching or activation is decreased. The individual bonding points have a rounded shape, which together with the pattern and the elastic and non-elastic component of the material decrease the risk for hole formation during activation of the material.

A line drawn between two centre points of two individual bonding points located closest to each other in the neighbouring rows of bonding points extending in the cross-direction may have an angle of from 30 to 75°, in respect of the extension of the cross-direction. In this way, the bonding points are not aligned, and positioned such that hole formation is further decreased.

Further, an angle between a line drawn between the centre point of an individual bonding point and the line of extension of the cross-direction may be from 30 to 60°, or from 40 to 50°, in respect of the extension of the cross-direction. Also in this way, the bonding points are not aligned, and positioned such that hole formation is further decreased.

The individual bonding points may have a circular shape. The individual bonding points may have an oval shape or the individual bonding points may have an elliptical shape. By the rounded shape, the forces occurring during stretching can be better spread within the whole area of the individual bonding point, whereby the risk for hole formation may be decreased.

In case the shape is oval or elliptical, each of the individual bonding points may have a longitudinal centre axis and a width axis which perpendicularly crosses the centre axis at the centre point of the bonding point, wherein the extension of the bonding point is longer along the longitudinal centre axis than along the width axis. Thus, an oblong shape for the individual bonding point may be received, and the bonding force may be increased.

The individual bonding points in the neighbouring rows of bonding points extending along the machine-direction may be angled differently in respect of the direction of the machine-direction and/or wherein the bonding points in the neighbouring rows of bonding points extending along the cross-direction are angled differently in respect of the direction of the cross-direction. In this way, a more "irregular" pattern can be obtained, which may be advantageous when decreasing the risk for hole formation. The bonding points in the neighbouring rows of bonding points extending along the machine-direction may be angled in mirror inverted angles in relation to each other and in respect of the machine-direction and/or wherein the bonding points in the neighbouring rows of bonding points extending along the cross-direction are angled in mirror inverted angles in relation to each other and in respect of the cross-direction. Thus, a more aesthetically pleasant appearance may be obtained.

The centre point of each bonding point in a row of bonding points extending in the cross-direction may be offset from a centre point of each bonding point in a neighbouring row of bonding points extending in the cross-direction, and wherein the centre points of at least two bonding points in two rows of bonding points extending in the machine-direction are aligned. In this way, it is possible to obtain several types of patterns.

The centre point of each bonding point in a row of bonding points extending in the machine-direction may be offset from a centre point of each bonding point in a neighbouring row of bonding points extending in the machine-direction, and wherein the centre points of at least two bonding points in two rows of bonding points extending in the cross-direction are aligned. Also in this way, it is possible to obtain several types of patterns.

The bonding points may be arranged such that they form a pattern comprising a series of hexagon-shapes in a repeated manner. Such bonding pattern further decreases the risk for hole formation during activation or stretching and is soft providing larger areas of nonwoven without bonding points and is aesthetically pleasant.

A bonding area obtained by the individual bonding points may be more than or at least 5% and up to and including 30%, or from 5-25%, or from 8-18% of the total area of the nonwoven material. In this way, sufficient area of the nonwoven is bonded while there are still areas without bonding points which thereby contribute to the softness of the material.

The amount of bonding points per unit area may be from 10 to 100 dots/cm$^2$, or from 20 to 70 dots/cm$^2$, or from 25 to 55 dots/cm$^2$.

The elastic polymeric material component may be comprised as a core material of a bi-component fiber and the non-elastic polymeric material component may be comprised as a sheath component of a bi-component fiber. In this way, only one fiber material is needed during manufacture.

The elastic polymeric material component may be comprised as a layer of nonwoven material in a layered nonwoven and the non-elastic polymeric material component may be comprised as another layer in a layered nonwoven. In this way, a material having different properties in different layers is obtained.

The non-elastic polymeric material component may comprise or consist of a polyolefin polymer. The polyolefin may be a polyethylene. The non-elastic polymeric material component may comprise or consist of a linear low density polyethylene having a melt index of 10-100 g/10 min, as measured at 190° C. with a 2.16 kg weight according to ASTM D1238 and a density of 0.92-0.97 g/cm$^3$, as measured according ASTM D792. The elastic polymeric material component may comprise or consist of a polyolefin polymer. The polyolefin may be a polyethylene. The elastic polymeric material component may comprise or consist of an ethylene-based block copolymer having a melt index of 5-30 g/10 min, as measured at 190° C. with a 2.16 kg weight according to ASTM D1238 and a density of 0.85-0.89 g/cm$^3$, as measured according ASTM D792. Such materials are economically viable.

The bonding pattern may be obtained by means of a calender means comprising a surface pattern providing the rows of individual bonding points. The pre-stretching or activation of the material may be obtained in a ring-rolling process. The ring-rolling process may be achieved in-line and in the machine-direction and/or in the cross-direction. The activation is performed in the opposite direction to the off-set of the bonding points. The material may thus be entered directly into the manufacturing process of the article. Thus, a simple manufacturing process for the nonwoven material may be obtained.

The elastic nonwoven material may be comprised at least in the rear panel of the absorbent article. In this way, the pulling up of the article is facilitated while the fit and comfort of the article are improved. To further improve the fit and comfort, the elastic nonwoven material may be further comprised in at least one of the front panel, side flaps, leg elastics or a belt of the absorbent article.

To provide a comfortable and durable product the basis weight of the nonwoven material may have a basis weight of from 10 to 40 g/m$^2$ or from 15 to 35 g/m$^2$.

The absorbent article may be a pant-type diaper for infants or adults.

Further aspects and features of the invention are described with reference to the detailed description and appended drawings.

BRIEF DESCRIPTION OF THE DRAWINGS

FIG. 1a schematically shows a front view of an exemplary embodiment of a pant-type absorbent article according to the present disclosure;

FIGS. 1b and 1c, respectively, schematically shows a rear view of two exemplary embodiments of the pant-type absorbent article shown in FIG. 1a comprising an elastic nonwoven material according to the present disclosure;

DETAILED DESCRIPTION OF PARTICULAR EMBODIMENTS

Figure 2:
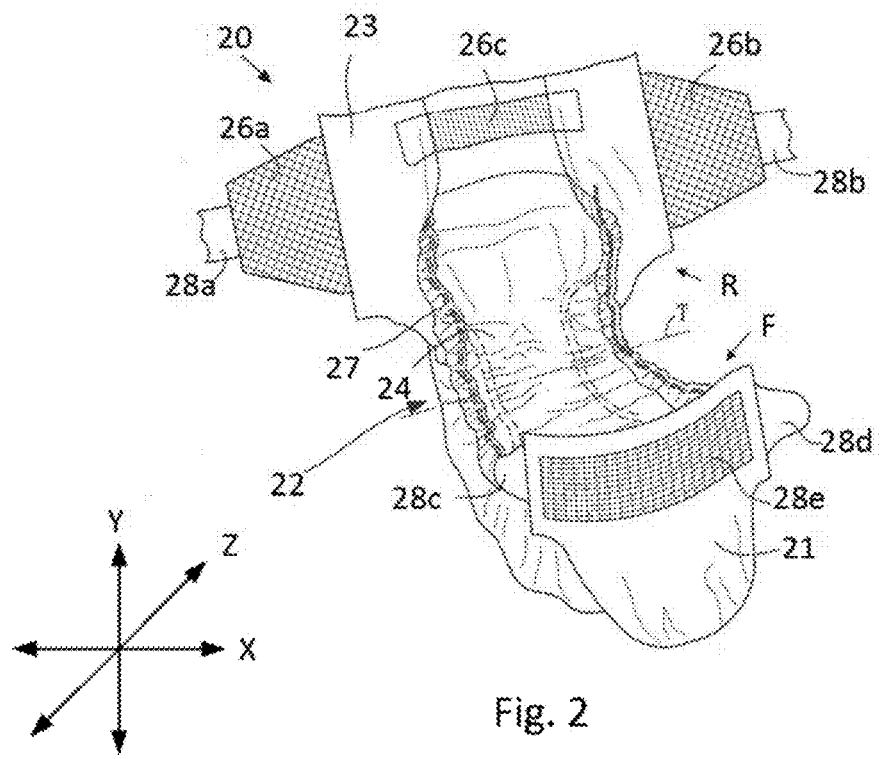
FIG. 2 shows schematically an exemplary embodiment of an open diaper comprising an elastic nonwoven material according to the present disclosure.

The absorbent article according to the present disclosure is adapted to be worn by a user and is thus a wearable absorbent article. The absorbent article comprises a front panel, a rear panel and an intermediate panel joining the front and the rear panels and optionally one or more fitting components for adapting the fit of the article to the body of a user. The fitting component or components may be included for example in the rear or front panels as separate or integrated elastic material components for adapting the fit of the product, leg elastics in the leg openings, side panels in open-type diapers or in a belt of a belted product. The absorbent article is aimed for single use and is thus disposable, wherein it is to be thrown away as waste after use. In absorbent articles of the present disclosure, such as diapers or adult incontinence articles, selected regions of the article may be provided with greater elasticity than other regions of the article.

According to the present disclosure, an elastic nonwoven material is comprised at least in one of the panels or a fitting component which can be for example, side panels, leg openings and a belt of an absorbent article. In this way, it is possible to provide an absorbent article with optimal fit and comfort. By elastic nonwoven material is meant a nonwoven material which may recover to its original shape after a force deforming, e.g. a force stretching the material during an activation step, is removed.

The absorbent article of the present disclosure is a pant type diaper or an open diaper, which may be belted, i.e. comprise a belt in the waist region for attaching the absorbent article to the body of the user. The absorbent article comprises an absorbent structure with an absorbent core in at least the crotch region of the article. The crotch region is arranged between the front and rear panels and is adapted to be placed so that it covers the crotch region of the user or wearer. Each of the panels have an inner surface facing a wearer's skin and an outer surface facing a wearer's garment, i.e. facing away from the wearer's skin. In this context, by the "inner surface" is also meant the side of the article facing the user.

To improve the fit of the article at least the rear panel may be elastically contractible in a waist circumferential direction. This may be attained by forming at least partially the inner surface of the rear panel of an elastic nonwoven material. In this way, the rear panel comprises an elastic nonwoven material, which material will be described more in detail below. The article comprises additionally the front panel, which panels may be integrated or separate panels connected to the intermediate panel comprising the crotch region. Thus, the front and rear panels may be separate pieces attached to the intermediate panel forming the crotch region. Alternatively, the front and rear panels may be integrated with the intermediate panel, for example by means of at least one common material layer which joins the panels.

The front panel is intended to overlie the abdominal region of the wearer and the rear panel is intended to overlie the lower back and buttocks region. The front and rear panels may cover the waist region of an absorbent article, which according to the present disclosure may include also the region sometimes referred to as a hip region which is the region below an upper part of the waist region and above the crotch region. The waist region generally thus includes the hips, the abdominal region and the lower part of the back and the upper parts of the buttocks that are at the same height as the hips. The crotch region extends between the front panel and the rear panel in a longitudinal direction of the article.

Examples of the absorbent articles are schematically shown in FIGS. 1a, 1b and 1c, FIG. 2 and FIG. 3. The absorbent article 10 of FIGS. 1a, 1b and 1c is a pant-type diaper or incontinence article and comprises a front panel 11 shown in FIG. 1a, a rear panel 13 shown in FIG. 1b and FIG. 1c and an intermediate panel 12 as shown in all of FIG. 1a-1c. The pant-type article 10 further comprises edge joining portions 15 which join the rear and front panels together in a longitudinal direction of the article. Before the article is joined together, the front panel 11, the intermediate panel 12 and the rear panel 13 may form an essentially H-shaped intermediate product in flattened condition (not shown), but the pant type article may also have other shapes. Pant-type products of different types are well known in the art. The longitudinal direction is schematically shown by the Y-axis, the transversal direction by the X-axis and the direction perpendicular to the plane of the longitudinal and transversal direction is shown by the Z-axis in FIG. 1a. Thereby a pair of leg openings LO and waist opening WO are formed. The rear panel 13 and the front panel 11 have an inner surface IS which is the side and/or surface of the article facing the skin of the user during the use of the article and an outer surface OS, which is the side and/or surface facing the garment of the user of the article as illustrated in FIG. 1a. The front panel 11 may comprise a front waist region of the article. The intermediate panel 12 joins the front 11 and rear 13 panels in the crotch region. These three panels 11, 13, 12 may be integrated to form a chassis of the absorbent article 10. The panels may comprise several layers of material. Usually, each of the front and rear panels comprises one or more layers of nonwoven materials and the intermediate panel comprises a liquid permeable topsheet material and a liquid impermeable backsheet material and an absorbent structure sandwiched there between.

The absorbent structure 14 is adapted to absorb bodily fluids, such as urine, and is attached by means of an adhesive. The absorbent structure 14 may extend across a crotch region in the intermediate panel 12 further into part of the front panel 11 and part of the rear panel 13.

The absorbent article according to the present disclosure comprises an elastic nonwoven material which is described more in detail below. In FIG. 1b the complete rear panel 13 comprises the elastic nonwoven material. In FIG. 1c the rear panel 13 partially comprises the elastic nonwoven material 132. Thus, the rear panel 13 may be at least partially formed of the elastic nonwoven material. The elastic nonwoven material may be provided in the form of a piece 132 of the elastic nonwoven material and may be comprised in proximity to an upper edge 133 of the body facing side of the rear panel 13 in which the waist opening is defined. The distance of the piece to the upper edge in the longitudinal direction of the absorbent article may vary depending on the size and purpose of the article and may be for example from about 5 to 100 mm, but is not limited thereto. The longitudinal direction means the direction of longer extension of the absorbent article, when the article is opened, for example before joining the sides by means of joining portions 15. In this way, the rear panel is rendered elastic and the article is easy to pull on and fits to the body of the user in a suitable way. The elastic nonwoven material may be attached for example with hot melt adhesives to the inner surface of the chassis. The size of the elastic nonwoven material piece 132 may vary, and may for example partially overlap the absorbent structure as shown in FIG. 1c. Also, the elastic nonwoven may extend along the whole extension of the transverse direction of the rear panel, i.e. the direction perpendicular to the longitudinal direction of the article. Additionally, or alternatively the front panel 11 in the chassis may comprise the elastic nonwoven material, whereby the elasticity of the article in a waist circumferential direction (WCD) of the article may be further improved. Also, the pair of leg openings may be provided with the elastic nonwoven material on the inner surface of the article. In this way, the elasticity of each region where the material is present is improved. Since at least one of the panels or fitting components are elastically contractible and comprises the elastic nonwoven material as described more in detail below, the absorbent article has a good fit to the body of the wearer while it is easy to pull up to the user position.

Figure 3:
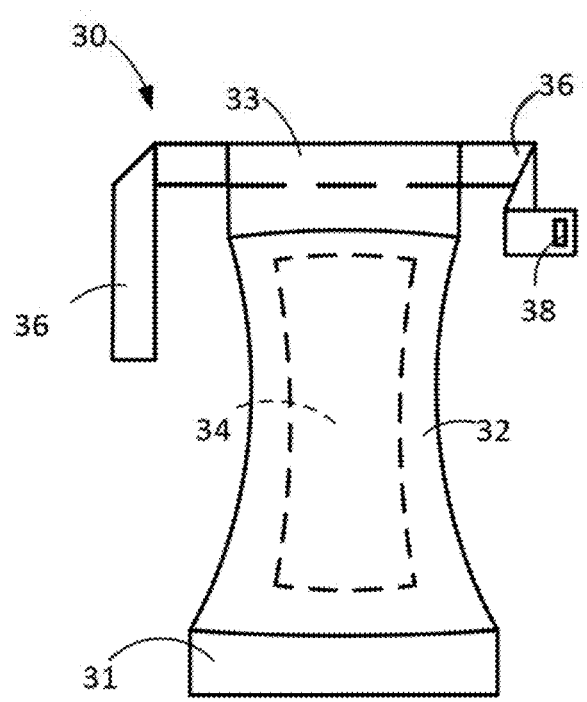
FIG. 3 shows schematically an exemplary embodiment of a belted open diaper comprising an elastic nonwoven material according to the present disclosure.

The absorbent article of the present disclosure may also be in the form of an open diaper as illustrated in FIGS. 2 and 3. The layers of the open diapers may be principally a liquid permeable topsheet located on the inner surface of the diaper, i.e. on the side facing towards the skin of the user, a backsheet located on the outer surface, i.e. on the side facing the garment of a wearer, and an absorbent structure sandwiched between the topsheet and the backsheet. Each of the diapers 20 and 30 comprises respectively a rear panel 23, 33, an intermediate panel 22, 32 and a front panel 21, 31, which may be provided as integrated material regions or as separate panels attached to each other.

Referring to FIG. 2 an open diaper 20, which may be aimed for infants or adults, is shown. The front panel 21 comprises an attachment area 28e for attachment means 28a and 28b, which are connected to a rear panel 23 via elastic side flaps 26a and 26b. On the transversal side of the attachment area 28e are a pair of non-elastic side flaps 28c and 28d that may be provided to facilitate accurate positioning of the diaper. The inner surface or side of the rear panel 23 may comprise a piece of elastic material 26c, which may be an elastic nonwoven material and may be of the type as described more in detail below. The pair of elastic rear side flaps 26a and 26b is provided to improve the fit of the article. The material of the elastic rear side flaps may also comprise or consist of the elastic nonwoven material as described more in detail below. The crotch region including an intermediate panel 22 comprises an absorbent structure 24, which extends along the longitudinal extension of the article, which is perpendicular to the transversal extension T illustrated in FIG. 2. The article 20 further comprises leg elastics 27 in the crotch region. The elastic nonwoven material that may be provided in the rear panel, on the inner surface thereof, improves the fit and the comfort of the article. In the illustrated example of FIG. 2, the diaper is in its relaxed state and thus forms a bowl-shape. It should be noted that the bowl shape may be straightened out when external force is provided to the article and the article is stretched into a flattened condition. In this way, the leg elastics and the rear portion are flattened, and the article extends in a longitudinal, transversal and thickness direction (X, Y, Z, illustrated in FIG. 2), wherein the thickness direction is perpendicular to the plane of the longitudinal and transversal extension of the article. Thus, the article does not form a bowl shape, but if the stretching force is released, the article returns to the bowl shape due to the elastic portions in the article.

In FIG. 3 a further example of an absorbent article is shown. The article is an open diaper 30 comprising a belt 36 extending on both transversal sides of the diaper. The belt 36 comprises an attachment means 38 for attachment to the belt or to the front panel 31 on the area of the front waist region. The article 30 further comprises a front panel 31, a rear panel 33, and an intermediate panel 32 which extends between the front 31 and the rear 33 panel 33, and the intermediate panel 32 is to be located in the crotch region of a wearer. An absorbent structure 34 is in the intermediate panel 32. The article 30 is illustrated from the side of an inner surface adapted to face a wearer's skin. The diaper may comprise an elastic nonwoven for example in the front panel 31, the rear panel 33, or in the intermediate panel 32 such as in the leg elastics (not shown) and/or in the belt 36 and the elastic nonwoven material may be of the kind described below.

Figure 4:
FIG. 4 schematically shows a side view of different layers of an exemplary embodiment of an absorbent article according to the present disclosure.

Typically, the absorbent structure may comprise or consist of an absorbent core and the structure is located primarily in the crotch region of the intermediate panel but may also extend partly into the front panel and the rear panel of the article. The absorbent structure and/or the absorbent core may comprise any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like. The absorbent structure is sandwiched between a liquid pervious top sheet and a generally liquid impervious backsheet. The outer cover, i.e. the backsheet of the chassis may also be the liquid impervious backsheet of the absorbent structure. The principal layers topsheet, absorbent structure and backsheet are schematically shown in FIG. 4. The topsheet 41 faces the skin of the wearer and the backsheet 43 faces the garment of the wearer and the absorbent structure 42 is sandwiched between the topsheet 41 and the backsheet 43.

By nonwoven material is meant a fabric material which is neither woven nor knit, but is instead made from a web of fibers interlocked with each other. The fibers need not to be prepared to yarns as in case of weaving or knitting. The fibers provided in the form of a sheet or web in which the fibers are held together by interlocking the fibers e.g. by mechanical interlocking of the fibers, by thermally fusing the fibers or by means of bonding the fibers together with a bonding agent or adhesive, such as starch, or synthetic resins.

The nonwoven material used in the present invention may be spunlaid, which is a manufacturing technique in which the web is formed by performing extrusion, spinning, drawing and supplying of fibers to form a web from a molten polymer in one continuous process. Fibers are spun and then directly dispersed into a web by e.g. deflectors or may be directed with air streams. Several variants of this concept are available, such as spunbond also referred to as spunbonded, meltblown and flash spinning process. In a spunbond process the nonwoven material is bonded after web forming by means of calender bonding. The nonwoven material may comprise or consist of spunbond nonwoven. The nonwoven material may comprise several nonwoven fabric layers, such as from two to six layers, for example two to three nonwoven fabric layers. All the layers may be spunbond nonwoven fabric layers, thereby forming e.g. a two-layer spunbond nonwoven material. One or two layers may be meltblown fabric layers, wherein the spunbonded nonwoven material is combined with a meltblown nonwoven and subsequently co-formed into a layered nonwoven material called SMS (spunbond-meltblown-spunbond). Meltblown nonwovens have extremely fine fiber diameters but are not strong fabrics. The nonwoven material of the present disclosure is bonded which may be performed by means of calender comprising a specific pattern of bonding points, whereby the risk for formation of holes during activation of the elastic nonwoven material is minimized.

The basis weight of the nonwoven material may be varied of from 5 to 80 g/m², or from 10 to 40 g/m², or from 15 to 35 g/m². When the basis weight is under 40 g/m², sufficient breathability, drapeability and comfort for the article may be obtained. The basis weight of from 15 to 35 g/m² may provide best comfort and flexibility while the processability of the material is still good.

The elastic nonwoven material of the present disclosure comprises a non-elastic polymeric material component and an elastic polymeric material component. By non-elastic polymeric material component is meant a component which may be stretched at a room temperature of 20° C. to at least twice the original length, but which does not return to the original length after the stretching force has been released. The non-elastic material component may decrease in length from about 10-15% of the stretched length after the stretching force has been released. By the elastic polymeric material component is meant a component which may be stretched at a room temperature of 20° C. to at least twice the original length, and which returns at least close to the original length after the stretching force has been released. Thus, the stretched length may decrease from 60-100% of the stretched length. For example, if the length of the material is 10 cm before stretching and 20 cm after stretching, the length of the material after the stretching force is released may thus be from 10-14 cm.

Figure 5A:
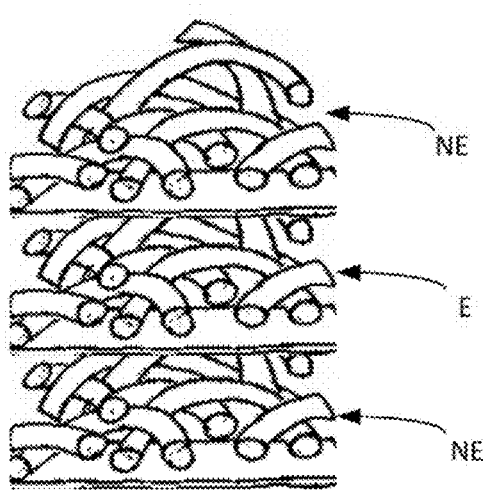
FIG. 5a schematically shows layers of a nonwoven material according to an exemplary embodiment of the present disclosure.
Figure 5B:
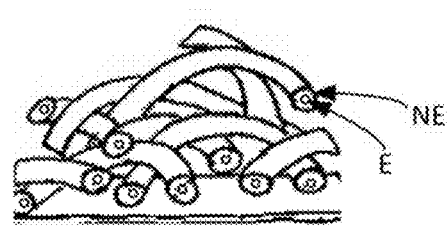
FIG. 5b schematically shows a nonwoven material comprising bi-component fibers according to an exemplary embodiment of the present disclosure.

The elastic component may be an elastic fiber or an elastic fiber component in a bi-component fiber. Similarly, the non-elastic component may be a non-elastic fiber or a non-elastic fiber component in a bi-component fiber. Alternatively, the elastic component may be an elastic nonwoven layer comprising elastic fibers in a multilayer nonwoven and the non-elastic component may be a non-elastic nonwoven layer comprising non-elastic fibers in a multilayer nonwoven. FIG. 5a illustrates schematically an elastic multilayer nonwoven material in which the uppermost and the lowermost layers are non-elastic NE and the middle layer sandwiched between the non-elastic layers is elastic E. The non-elastic layer and the fibers in the layers may be stretchable to minimize the risk for formation of holes. In FIG. 5b is an embodiment illustrated in which the elastic nonwoven material comprises bi-component fibers having a core-sheath type of structure in which the core component is elastic E and the sheath component is non-elastic NE.

The non-elastic component may be a polyolefin based polymeric material such as polyethylene and may comprise or consist of a linear low density polyethylene having a melt index of 10-100 g/10 min, as measured at 190° C. with a 2.16 kg weight according to ASTM D1238. The non-elastic polymeric material component may have a density of for example 0.92-0.97 g/cm³, as measured according ASTM D792.

The elastic component may be a polyolefin based polymeric material such as polyethylene, and may comprise or consist of an ethylene-based block copolymer having a melt index of 5-30 g/10 min, as measured at 190° C. with a 2.16 kg weight according to ASTM D1238. The elastic polymeric material component may have a density of for example 0.85-0.89 g/cm³, as measured according ASTM D792. Examples of resins with these characteristics are ASPUN™ 6850 and INFUSE™ 9900, both from the Dow Chemical Company. These elastic materials mentioned above are more economically viable than the materials used in prevailing technology which are based on polyurethane elastic fibers.

Figure 6:
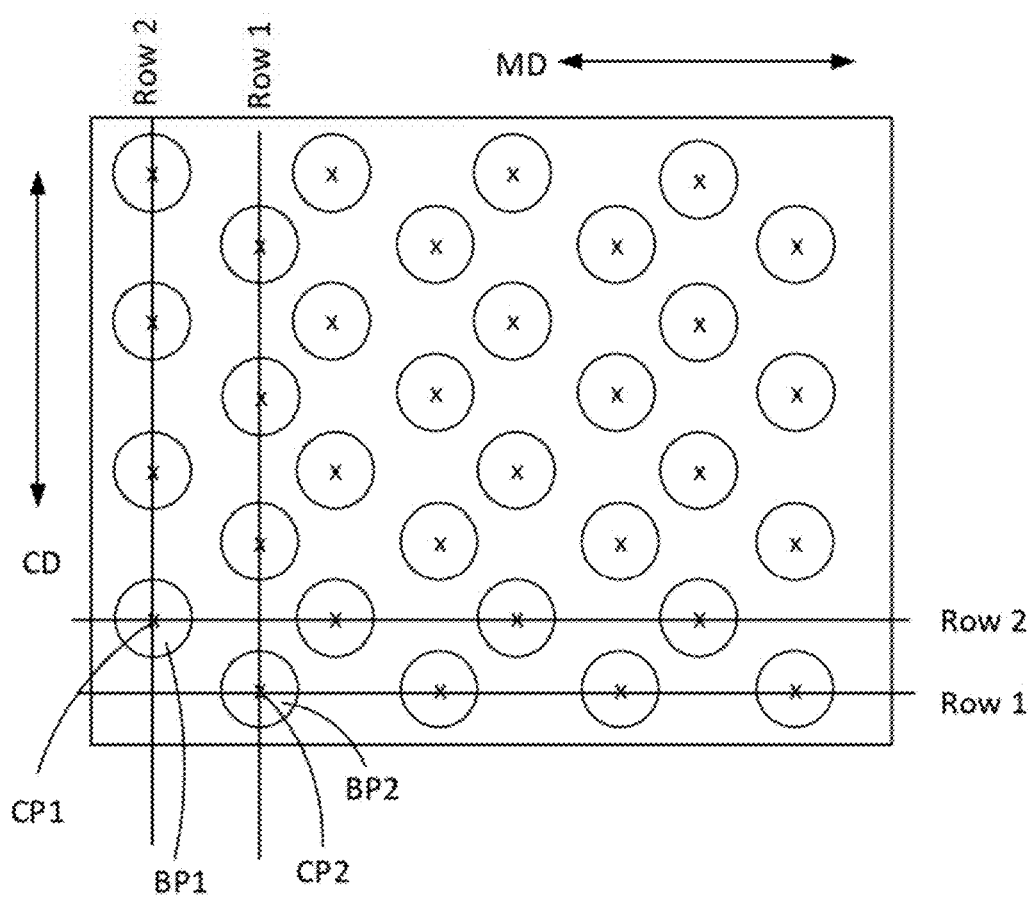
FIG. 6 shows schematically an exemplary embodiment of a bonding pattern in an elastic nonwoven material useable in the absorbent article of the present disclosure.
Figure 7:
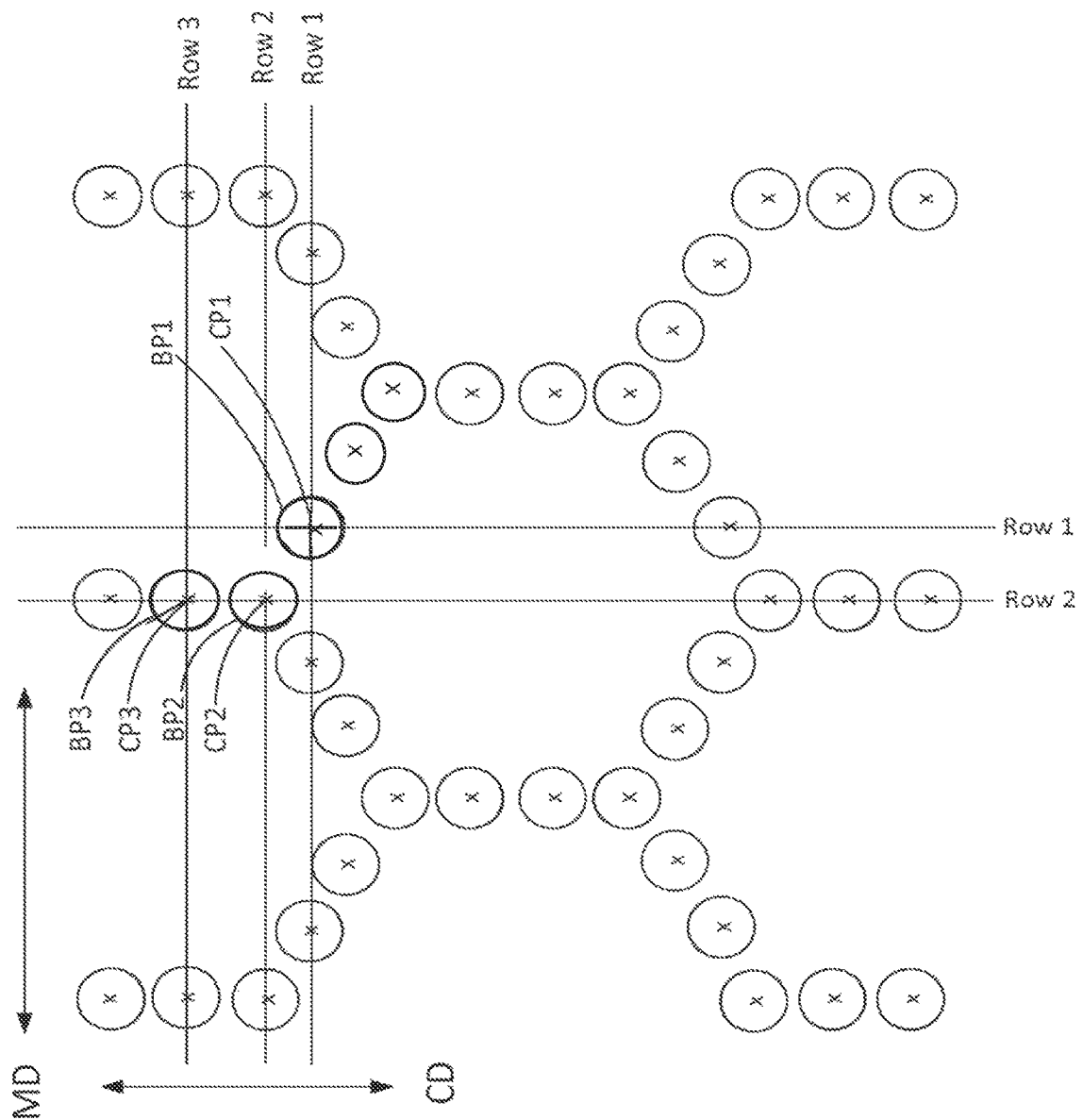
FIG. 7 shows schematically another exemplary embodiment of a bonding pattern in an elastic nonwoven material useable in the absorbent article of the present disclosure.
Figure 8:
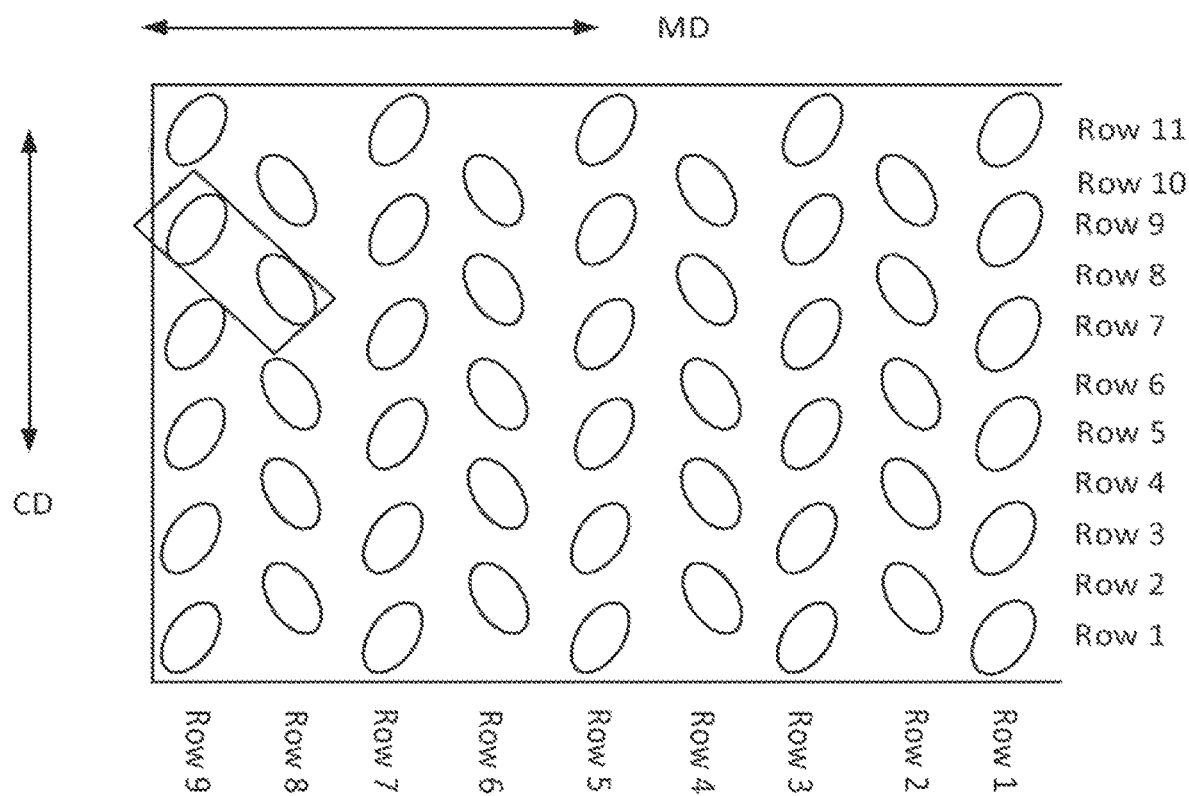
FIG. 8 shows schematically another exemplary embodiment of a bonding pattern in an elastic nonwoven material useable in the absorbent article of the present disclosure.

The elastic nonwoven material is bonded by means of bonding points, which are individual and/or distinct and arranged in a specific bonding pattern, exemplary embodiments of which are illustrated in FIGS. 6, 7 and 8. The bonding points are arranged in rows of individual bonding points extending in a machine-direction and a cross-direction of the nonwoven material. By machine-direction is meant the running direction of the manufacturing machine and by cross-direction the direction perpendicular to the machine-direction. The different directions are schematically shown in FIG. 6 to FIG. 8.

Referring to FIG. 6, each of the individual bonding points BP, only two of which are indicated, has a centre point CP. Generally, the pattern comprises rows of individual bonding points extending in a machine-direction and a cross-direction of the nonwoven material, wherein the centre point of each bonding point is offset from a centre point of each bonding point in a neighbouring row of bonding points extending in the cross-direction and in the machine-direction, respectively. By offset from is meant that the centre points are not aligned or not arranged in parallel in respect of a line extending in the machine-direction or cross-direction and drawn between the centre points of bonding points in the rows of bonding points. The bonding points have a rounded shape. Due to the specific pattern and the rounded shape of the individual bonding points, the risk for formation of holes during activation in the machine-direction is then substantially reduced.

In FIG. 6 bonding points offset from each other are illustrated by means of circular bonding points. The bonding points have a rounded shape and may thus be for example circular, oval or elliptical. As can be seen, the pattern consists of bonding points which are arranged such that the centre point CP1 of each bonding point BP1 in a Row 1 of bonding points extending in the cross-direction CD and machine-direction MD is offset from, and thus non-aligned with a centre point CP2 of each bonding point BP2 in a neighbouring Row 2 of bonding points extending in the cross-direction CD and in the machine-direction MD. It has surprisingly been noted that by arranging the bonding points with a rounded shape and centre points of the bonding points offset from each other in the neighbouring rows, the risk for formation of holes during the activation, i.e. stretching, of the nonwoven material is reduced. The bonding points, with a rounded shape, are arranged with the centre points of the bonding points offset from the centre points of the bonding points in the neighbouring rows in the cross-direction of the material. The risk for formation of holes during activation in the machine-direction is then substantially reduced.

FIG. 7 shows a pattern comprising rows of individual bonding points having a circular shape and extending in a machine-direction MD and a cross-direction CD of the nonwoven material. The bonding points are arranged such that the centre point CP1 of the bonding point BP1 in a Row 1 of bonding points extending in the cross-direction CD is offset from, and thus non-aligned with a centre point CP2 of the bonding point BP2 in a neighbouring Row 2 of bonding points extending in the cross-direction CD. Correspondingly, the bonding points are arranged such that the centre point CP1 of the bonding point BP1 in a row 1 of bonding points extending in the machine-direction MD is offset from, and thus non-aligned with a centre point CP2 of the bonding point BP2 in a neighbouring row 2 of bonding points extending in the machine-direction MD. The pattern in FIG. 7 however comprises also rows of bonding points extending in the machine-direction MD in which the bonding points are aligned. For example, as shown in FIG. 7 the centre point CP2 of the bonding point BP2 in Row 2 of bonding points extending in the machine-direction MD is not offset from, and is thus aligned with a centre point CP3 of the neighbouring bonding points BP3 in a neighbouring row of bonding points indicated as Row 3 extending in machine-direction MD. However, as defined in the present claim 1, each bonding point in a row of bonding points extending in the cross-direction CD is offset from a centre point of each bonding point in a neighbouring row of bonding points extending in the cross-direction, respectively. In this way, the circular bonding points may form a pattern comprising a plurality or series of hexagon-shaped sub-patterns. By sub-pattern is meant the individual shapes formed by several individual bonding points, which in this case are hexagons. By the pattern comprising the series of hexagons an elastic nonwoven having decreased risk for formation of holes during stretching of the material in the machine-direction is obtained while the material is soft and the appearance of the material is aesthetically pleasant.

Figure 9:
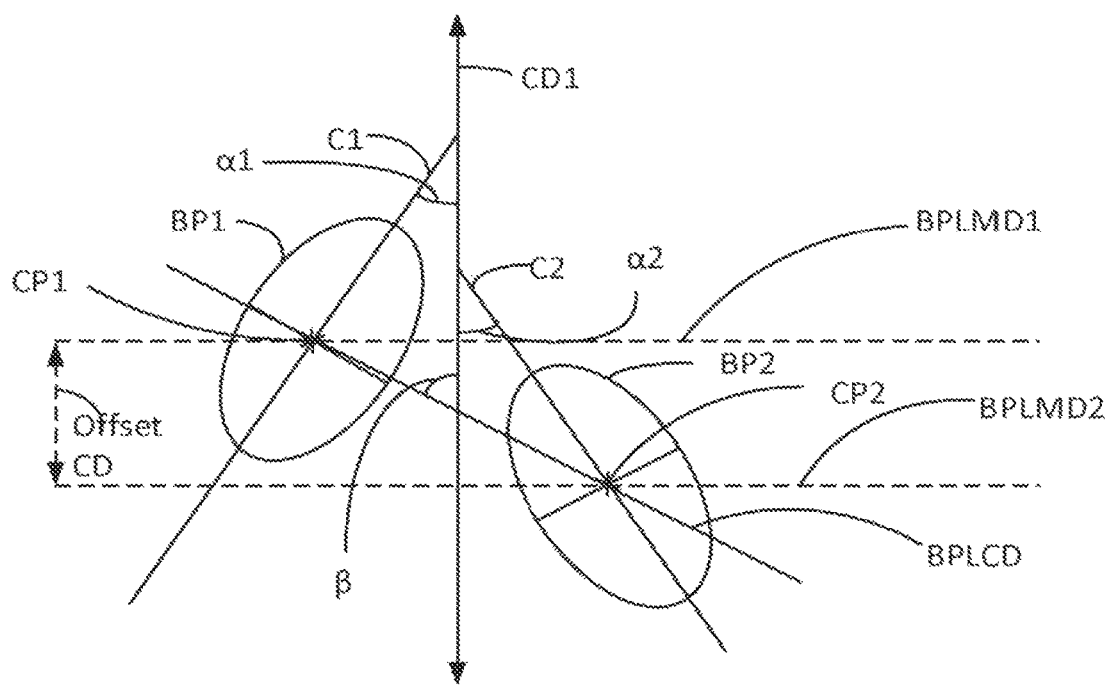
FIG. 9 shows an enlargement of two neighbouring bonding points from FIG. 8 with a line extending in a cross-direction between the bonding points.

In FIG. 8 the bonding points have an elliptical shape and are thus rounded. The individual bonding points extend in rows in the machine-direction MD and cross-direction CD of the nonwoven material. The rows extending in cross-direction are shown as Row 1 to Row 11. FIG. 9 shows an enlargement of two individual bonding points BP1 and BP2 in the neighbouring rows of bonding points. In this example the relation of the bonding points to the cross-direction CD is shown and described, but the relation to the machine-direction is analogously corresponding.

As can be seen from FIG. 9, each of the individual bonding points BP1 and BP2 has a respective centre point CP1 and CP2. The centre point CP1 of the bonding point BP1, which in the exemplary embodiment is in the row 9 of bonding points extending in the cross-direction, is offset from, i.e. non-aligned with a centre point CP2 of the bonding point BP2 in a neighbouring row 8 of bonding points extending in the cross-direction. As can be seen, a line BPLCD drawn between the centre points CP1 and CP2, has an angle β in respect of a line CD1 drawn between the centre points in the direction of the cross-direction CD. The angle β is smaller than 90°. The angle may be from 30 to 75°, such as from 40 to 60°. If the angle were 90°, it would indicate that the centre points are aligned and thus not offset from each other. Also, lines BPLMD1 and BPLMD2 drawn through the respective centre points CP1 and CP2 in machine-direction MD are distanced in the cross-direction CD from each other with a distance marked Offset CD, which also indicates that the centre points of the bonding points are offset from each other. Similarly, if the lines BPLMD1 and BPLMD2 were coinciding, it would indicate that the centre points are aligned and thus not offset from each other, but since this is not the case, the bonding points are offset from each other.

Further, the longitudinal extension of an oval or elliptical bonding point may be angled in respect of the cross-direction or machine-direction. The shape of the oval or elliptical bonding points is oblong and each of the individual bonding points has a longitudinal centre axis and a width axis which perpendicularly crosses the centre axis with a centre at the centre point of the bonding point. The extension of the bonding point is longer along the longitudinal centre axis than along the width axis. The width of the oblong oval or elliptical bonding points varies along the longitudinal extension of the longitudinal centre axis, for example so that the extension is a mirror-image in respect of the width axis on each longitudinal side of the centre point.

In FIG. 9 an exemplary embodiment is shown in which an angle α1 or α2 between a line C1 or C2, respectively, drawn between the respective centre point CP1 or CP2 of the individual bonding point BP1 or BP2 in the direction of the longitudinal centre axis and the line CD1 extending in the direction of the extension of the cross-direction CD may be of from 30 to 60°, or 40 to 50°, in respect of the extension of the cross-direction. By arranging the bonding points so that the longitudinal extension is angled in respect of the cross-direction at an angle of less than 90°, the formation of holes during the activation may be further decreased.

According to an exemplary embodiment the individual bonding points BP1 and BP2 in the neighbouring rows of bonding points extending along the machine-direction may be angled differently in respect of the direction of the machine-direction MD and/or the bonding points BP1 and BP2 in the neighbouring rows of bonding points extending along the cross-direction CD may be angled differently in respect of the direction of the cross-direction CD. By using different angles, the formation of holes may be further reduced. The bonding points BP1 and BP2 in the neighbouring rows of bonding points extending along the machine-direction may be angled in mirror inverted angles α1 and α2 in relation to each other and in respect of the machine-direction and/or wherein the bonding points in the neighbouring rows of bonding points extending along the cross-direction may be angled in mirror inverted angles α1 and α2 in relation to each other and in respect of the cross-direction CD, as shown in FIG. 8. In this way, a homogenous structure for the nonwoven material may be obtained.

A bonding area obtained by the individual bonding points may be more than or at least 5% and up to and including 30%, or from 5-25%, or from 8-18% of the total area of the nonwoven material. In this way, a sufficiently bonded material may be obtained, while the risk for hole formation may be reduced. The amount of bonding points per unit area may be from 10 to 100 dots/cm$^2$, or from 20 to 70 dots/cm$^2$, or from 25 to 55 dots/cm$^2$.

The bonding pattern may be obtained by means of a calender means comprising for example a compression cylinder with a surface pattern providing the pattern of individual bonding points. According to the present disclosure, the specific bonding pattern reduces the risk of formation of holes during the activation step of the elastic material. In certain embodiments, the activation step is a necessary process step which optimizes the elastic properties of the elastic material. During the activation step, the elastic nonwoven material is pre-stretched before joining with the rest of the absorbent article and may be performed e.g. by means of intermeshing gears or "ring-rolling" process step, which are well known in the art. Before attaching the material to an absorbent article, the material is pre-stretched. The stretching may be performed in cross-direction or the machine-direction or a combination. The stretch ratio, i.e. the length of the stretched material in the stretching direction compared to the length of the material in relaxed state, may be from 50-300%. Further material layers may then be attached to the elastic nonwoven material in the pre-stretched state during the manufacture of an absorbent article.

The topsheet material and the backsheet material may comprise a non-elastic nonwoven material. The liquid permeable topsheet may comprise or consist of a nonwoven material which is spunbonded, meltblown, carded, hydroentangled, wetlaid, etc. which may be composed of natural fibers, such as woodpulp or cotton fibers, synthetic fibers, such as polyester, polyethylene, polypropylene, viscose, etc. or from a mixture thereof. The topsheet material may further be composed of tow fibers, porous foams, apertured plastic films etc. The materials suited as topsheet materials should be soft and non-irritating to the skin and be liquid permeable so that it may be readily penetrated by body fluid, e g urine, and display low rewetting properties.

The liquid impermeable backsheet may comprise or consist of a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent core, while still preventing liquids from passing through the backsheet material.

The top sheet and backsheet may be connected to each other for example by adhesive bonding, gluing or welding by heat or ultrasonic. The topsheet and/or the backsheet may further be attached to the absorbent structure or core by any method known in the art, such as adhesive, heat-bonding etc.

EXAMPLES

Figure 10:
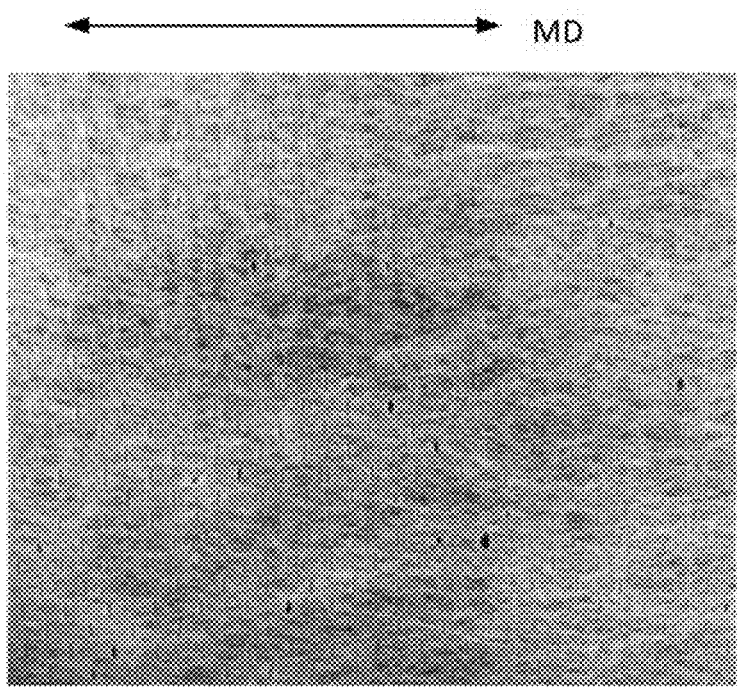
FIG. 10 shows an enlarged detailed photograph of an elastic nonwoven material with another type of bonding points after the activation step.

In the examples, two elastic nonwoven materials with different bonding patterns were pre-stretched in the machine-direction. The bonding patterns for the materials are described below:

The bonding pattern in FIG. 10, hereafter referred to as "CD-Rod", comprises line-shaped individual bonding points arranged in rows of bonding points extending in a cross-direction of the material. The individual line-shaped bonding points are aligned with the individual bonding points in a neighboring row of bonding points in the cross-direction, but not in the machine-direction. The material has a bonding area of 10% of the total area of the nonwoven material and the bonding point density is 9 dots/cm$^2$. The dot size of each individual bonding point is 1.11 mm$^2$.

Figure 11:
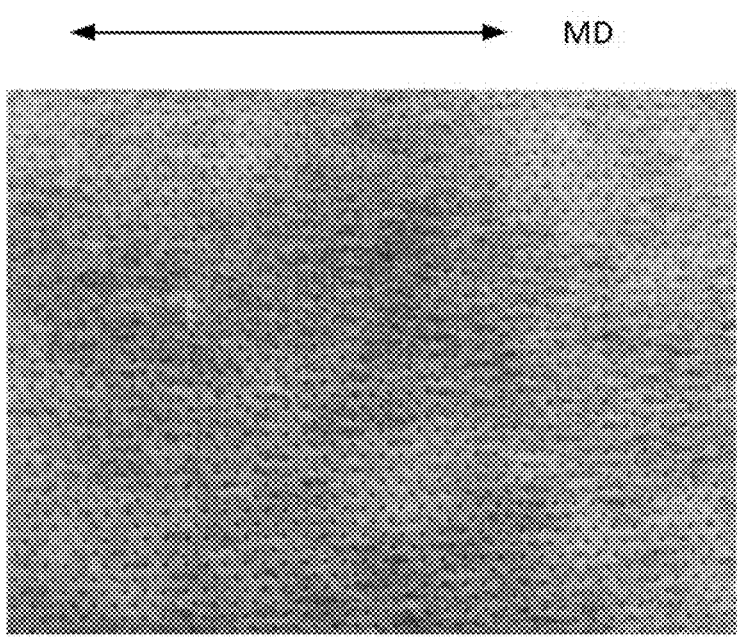
FIG. 11 shows an enlarged detailed photograph of an exemplary elastic nonwoven material according to the present disclosure after the activation step.

The bonding pattern in FIG. 11 hereafter referred to as "oval elliptic" corresponds to the pattern as shown in FIG. 8. The material is bonded by means of rows of individual bonding points extending in a machine-direction and a cross-direction. The bonding points are elliptical and the centre point of each bonding point in a row of bonding points extending in the cross-direction and machine-direction is offset from a centre point of each bonding point in a neighbouring row of bonding points extending in the cross-direction and in the machine-direction. The material has a bonding area of 18% of the total area and the bonding point density is 50 dots/cm$^2$. The dot (individual bonding point) size is 0.36 mm$^2$.

The elastic nonwoven material in both examples comprises bi-component fibers with the outer component of a linear low density polyethylene with density of 0.935 g/cm$^3$ and a melt index of 19 g/10 min @2.16 kg (ASTM D1238). The inner component of the fiber is an ethylene based block copolymer with a density of 0,877 g/cm$^3$ and a melt index of 15 g/10 min @2.16 kg (ASTM D1238) (INFUSE™ 9817 supplied by the Dow Chemical Company). The nonwoven is spunbond. After bonding the material, it was activated by stretching in the machine-direction by using a ring-rolling process to a stretch level of 150%.

As can be seen from the photograph in FIG. 11 the bonding pattern according to the present disclosure comprising bonding points with rounded shape minimizes the risk for hole initiation.

As can be seen in FIG. 10, activation of material with a bonding pattern with line-shaped bonding points creates holes in the material. In contrast as seen in FIG. 11, the non-woven material survives activation and no holes are created with a bonding pattern according to the present disclosure.

The invention claimed is:

1. A pant diaper comprising:
a front panel and a rear panel, wherein the front panel and the rear panel are joined directly to each other at side seams, and
an intermediate panel joined to the front and the rear panels between the front and rear panels, wherein the intermediate panel is a separate panel that is joined to the front and rear panels,
each of the panels having an inner surface facing a wearer's skin and an outer surface facing the wearer's garment, wherein at least one of the front and rear panels is elastically contractible and comprises an elastic nonwoven material,
wherein the elastic nonwoven material is pre-stretched and comprises a non-elastic polymeric material component and an elastic polymeric material component comprised in a form of fibers,
wherein the elastic nonwoven material is bonded by means of individual bonding points arranged in a pattern, wherein the pattern comprises rows of individual bonding points extending in a machine-direction and a cross-direction of the elastic nonwoven material,
wherein each of the individual bonding points has a centre point and the centre point of each individual bonding point in a row of individual bonding points extending in the cross-direction is offset from a centre point of each individual bonding point in a neighbouring row of individual bonding points extending in the cross-direction, and
each of the individual bonding points in a row of individual bonding points extending in the machine-direction is offset from a centre point of each individual bonding point in a neighbouring row of individual bonding points extending in the machine-direction,
wherein:
the elastic nonwoven material is pre-stretched in the machine direction,
the elastic nonwoven material extends from one of the side seams to another of the side seams in at least one of the front and rear panels, and
the side seams comprise the elastic nonwoven material.

2. The pant-type diaper according to claim 1, wherein a line drawn between two centre points of two of the individual bonding points located closest to each other in the neighbouring rows of bonding points extending in the cross-direction has an angle of from 30 to 75° with respect to the cross-direction.

3. The pant diaper according to claim 1, wherein the individual bonding points are oval in shape, and an angle between a line drawn along a major axis of the bonding points and through the centre point of an individual one of the bonding points extends at an angle from 30 to 60° with respect to the cross-direction.

4. The pant diaper according to claim 1, wherein the individual bonding points have a shape selected from an oval shape and an elliptical shape.

5. The pant diaper according to claim 4, wherein the shape is elliptical, and each of the bonding points has a longitudinal centre axis and a width axis which perpendicularly crosses the centre axis at the centre point of the individual bonding point, wherein an extension of the individual bonding point is longer along the longitudinal centre axis than along the width axis.

6. The pant diaper according to claim 5, wherein the individual bonding points in one of the rows of individual bonding points extending along the machine-direction are angled differently than the individual bonding points extending in a neighboring row.

7. The pant diaper according to claim 5, wherein the individual bonding points in the neighbouring rows of individual bonding points extending along the machine-direction are angled in mirror inverted angles in relation to each other and in respect of the machine-direction or wherein the individual bonding points in the neighbouring rows of individual bonding points extending along the cross-direction are angled in mirror inverted angles in relation to each other and in respect of the cross-direction.

8. The pant diaper according to claim 4, wherein the centre point of each individual bonding point in a row of individual bonding points extending in the cross-direction is offset from a centre point of each individual bonding point in a neighbouring row of individual bonding points extending in the cross-direction, and wherein the centre points of at least two individual bonding points in two rows of individual bonding points extending in the machine-direction are aligned.

9. The pant diaper according to claim 4, wherein the centre point of each individual bonding point in a row of individual bonding points extending in the machine-direction is offset from a centre point of each individual bonding point in a neighbouring row of individual bonding points extending in the machine-direction, and wherein the centre points of at least two individual bonding points in two rows of individual bonding points extending in the cross-direction are aligned.

10. A pant diaper comprising:
a front panel and a rear panel, wherein the front panel and the rear panel are joined directly to each other at side seams, and
an intermediate panel joined to the front and the rear panels between the front and rear panels,
each of the panels having an inner surface facing a wearer's skin and an outer surface facing the wearer's garment, wherein at least one of the front and rear panels is elastically contractible and comprises an elastic nonwoven material,
wherein the elastic nonwoven material is pre-stretched and comprises a non-elastic polymeric material component and an elastic polymeric material component comprised in a form of fibers,
wherein the elastic nonwoven material is bonded by means of individual bonding points arranged in a pattern, wherein the pattern comprises rows of individual bonding points extending in a machine-direction and a cross-direction of the elastic nonwoven material,
wherein each of the individual bonding points has a centre point and the centre point of each individual bonding point in a row of individual bonding points extending in the cross-direction is offset from a centre point of each individual bonding point in a neighbouring row of individual bonding points extending in the cross-direction, and
each of the individual bonding points in a row of individual bonding points extending in the machine-direction is offset from a centre point of each individual bonding point in a neighbouring row of individual bonding points extending in the machine-direction,
wherein:
the elastic nonwoven material is pre-stretched in the machine direction,
the elastic nonwoven material extends from one of the side seams to another of the side seams in at least one of the front and rear panels, and
the individual bonding points are arranged such that they form a shape of a hexagon in a repeated manner.

11. The pant diaper according to claim 1, wherein a bonding area obtained by the individual bonding points is more than or at least 5% of the total area of the nonwoven material.

12. The pant diaper according to claim 1, wherein an amount of individual bonding points per unit area is from 10 to 100 dots/cm$^2$.

13. The pant diaper according to claim 1, wherein the elastic polymeric material component is comprised as a core material of a bi-component fiber and the non-elastic polymeric material component is comprised as a sheath component of a bi-component fiber.

14. The pant diaper according to claim 1, wherein the elastic polymeric material component is comprised as a layer of nonwoven material in a layered nonwoven and the non-elastic polymeric material component is comprised as another layer in a layered nonwoven.

15. The pant diaper according to claim 1, wherein the elastic polymer material component comprises polyolefins.

16. The pant diaper according to claim 1, wherein the elastic polymeric material component comprises or an ethylene-based block copolymer having a melt index of 5-30 g/10 min, as measured at 190° C. with a 2.16 kg weight and a density of 0.85-0.89 g/cm$^3$.

17. The pant diaper according to claim 1, wherein the bonding pattern is obtained by means of a calendar means comprising a surface pattern providing the rows of individual bonding points.

18. The pant diaper according to claim 1, wherein the pant-type diaper is for adults.

19. The pant diaper according to claim 1, further comprising one or more fitting components for adapting the fit of the article to a body of a user.

20. The pant diaper according to claim 1, wherein when the centre points of the bonding points are closer to each other in the rows extending in the cross-direction than the centre points in the rows extending in the machine direction.

21. The pant diaper according to claim 1, wherein an entirety of the front and rear panels are comprised of the elastic nonwoven material.

22. The pant diaper according to claim 5, wherein the individual bonding points in one of the rows of individual bonding points extending along the cross-direction are angled differently than the individual bonding points extending in a neighboring row.

23. The pant diaper according to claim 1, wherein the pant-type diaper is for infants.

24. The pant diaper according to claim 1, wherein at least the rear panel is elastically contractible in a waist circumferential direction.

25. The pant diaper according to claim 21, wherein the elastic nonwoven material extends from one of the side seams to another of the side seams in both of the front and rear panels.

26. The pant diaper according to claim 1, wherein the elastic nonwoven material comprises bi-component fibers having a core-sheath structure in which the core component is elastic and the sheath component is non-elastic.

27. The pant diaper according to claim 1, wherein the elastic nonwoven material comprises an elastic nonwoven layer sandwiched between two non-elastic nonwoven layers.

28. The pant diaper according to claim 1, wherein the elastic nonwoven material is attached to the inner surface of the at least one of the front and rear panels.

29. The pant diaper according to claim 1, wherein the elastic nonwoven material is attached to the inner surface of the at least one of the front and rear panels while the elastic nonwoven material is pre-stretched.

30. The pant diaper according to claim 1, further comprising an absorbent core and wherein the elastic nonwoven material is attached to the inner surface of the at least one of the front and rear panels and partially overlaps the absorbent core.

31. The pant diaper according to claim 1, wherein the intermediate panel is made from a different material than the front and rear panels.

32. The pant diaper according to claim 1, wherein the pant diaper is a pull-on diaper having pre-formed waist and leg openings.

\* \* \* \* \*